United States Patent [19]

Jayne et al.

[11] 4,002,568

[45] Jan. 11, 1977

[54] LUBRICATING OIL COMPOSITIONS

[75] Inventors: Gerald John Joseph Jayne; Herbert Frank Askew, both of Wokingham, England

[73] Assignee: Edwin Cooper and Company Limited, Bracknell, England

[22] Filed: Oct. 3, 1974

[21] Appl. No.: 511,920

[30] Foreign Application Priority Data

Oct. 4, 1973 United Kingdom ............ 46372/73

[52] U.S. Cl. .................................. 252/46.7; 252/46.6; 252/78.5; 252/400 A; C10M/5/24; C10M/7/46

[51] Int. Cl.$^2$ ..................... C10M 1/48; C10M 3/42

[58] Field of Search .................. 252/46.6, 46.7, 78, 252/400 A

[56] References Cited

UNITED STATES PATENTS

| | | | |
|---|---|---|---|
| 3,482,002 | 12/1969 | Dever et al. | 252/46.6 |
| 3,687,848 | 8/1972 | Colclough et al. | 252/46.6 |
| 3,795,613 | 3/1974 | Hotten | 252/46.7 |
| 3,878,194 | 4/1975 | Moffatt et al. | 252/46.6 |

*Primary Examiner*—Delbert E. Gantz
*Assistant Examiner*—I. Vaughn
*Attorney, Agent, or Firm*—Donald L. Johnson; Robert A. Linn; Joseph D. Odenweller

[57] ABSTRACT

New compounds are derived from intra-molecular and inter-molecular, in the case of a polymer, sulphur bridged hydrocarbon rings of 12 carbon atoms. The hydrocarbon ring is preferably 1,5,9-cyclododecatriene. The compound also contains the residue of a dithiophosphoric acid containing two organic moieties. The new compounds are useful in major or minor amounts in lubricating oil compositions. The lubricating oil may be a hydraulic oil. The composition may also contain other conventional lubricant additives.

7 Claims, No Drawings

LUBRICATING OIL COMPOSITIONS

This invention relates to lubricating oil compositions and also to new compounds useful in such lubricating oil compositions.

According to the present invention there is provided a compound of the formula

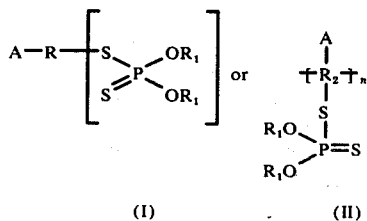

wherein in Formula (I) R is the residue of an intramolecular sulphur bridged hydrocarbon ring containing 12 carbon atoms or wherein in Formula (II) $\text{-}(R_2)_n\text{-}$ is a polymer comprising the residue of a plurality of substantially intermolecularly sulphur-bridged hydrocarbon rings each containing 12 carbon atoms, n being the degree of polymerisation, each $R_1$ is the same or different and is an alkyl, alkenyl, aryl, alkaryl or aralkyl group having from 2 to 18 carbon atoms, preferably 3 to 18 carbon atoms, and A is a nucleophilic group.

In a further aspect the present invention provides a lubricating composition comprising a lubricating oil and a compound of the formula

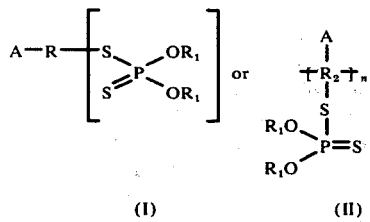

wherein in Formula (I) R is the residue of an intramolecular sulphur bridged hydrocarbon ring containing 12 carbon atoms or wherein in Formula (II) $\text{-}(R_2)_n\text{-}$ is a polymer comprising the residue of a plurality of substantially intermolecularly sulphur bridged hydrocarbon rings each containing 12 carbon atoms, n being the degree of polymerisation, each $R_1$ is the same or different and is an alkyl, alkenyl, aryl, alkaryl, or aralkyl group having from 2 to 18 carbon atoms, preferably 3 to 18 carbon atoms, and A is a nucleophilic group.

In one aspect of the present invention the composition comprises a major amount of the lubricating oil and a minor amount of a compound of the Formula (I) or (II).

R, (or $R_2$) may particularly be derived from 1,5,9-cyclododecatriene especially the cis-trans-trans version thereof. The sulphur bridging of these hydrocarbons is achieved by reacting with sulphur dichloride or other sulphur chloride compound to yield either monomeric or polymeric derivatives.

The group A preferably has the formula

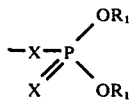

wherein each $R_1$ is the same or different and is as described above and each X is the same or different and is oxygen or sulphur. Alternatively, the group A may have the formula - $XR_3$ or

wherein X is as defined above and $R_3$ is an alkyl, aryl, alkaryl or aralkyl group. Further alternatives for A include -CN, -NCO and -NCS.

The group

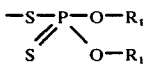

will be recognizable as the residue of a dithiophosphoric acid.

The two organic moieties present in each molecule of dithiophosphoric acid, which moieties constitute the groups, $R_1$ can be chosen in accordance with the criteria commonly adopted in dithiophosphate additives. That is to say the organic moieties should be of sufficient size and sufficiently hydrocarbon in nature to impart the desired degree of oil-solubility. However, the organic moieties desirably should not be so large that the phosphorus and sulphur content of the additive is undesirably small, in terms of weight, as this creates a need for large dosage weights to be used in lubricants in order to impart the required degree of antioxidant and antiwear/load carrying properties. Within the foregoing criteria, one may select the organic moieties from among the very wide variety of organic groups known in the art as suitable for inclusion in dithiophosphoric acids. Thus the organic moieties may be alkyl, alkenyl, aryl, alkaryl or aralkyl groups, and optionally may bear one or more unreactive substituents such as alkoxy groups.

Preferably each organic moiety is an alkyl, phenyl or alkyl-substituted phenyl group. The alkyl-substituted phenyl group may contain from 7 to 18 carbon atoms. Most preferably, however, each organic moiety is an alkyl group containing from 3 to 10 carbon atoms. The two organic moieties may be the same. alternatively, a mixture of organic moieties can be employed by using a dithiophosphoric acid containing two different organic groups and/or by using a mixture of two or more different dithiophosphoric acids.

As is well known in the art dithiophosphoric acids may be prepared by reacting hydroxy-substituted organic compounds, for example alcohols, phenols, alkyl substituted phenols or mixtures thereof, with phosphorus pentasulphide in approximately 4 to 1 molar ratio.

The novel compounds used in the lubricating compositions of the present invention may be prepared by reacting a dithiophosphoric acid, or a metal e.g., sodium or an amine salt thereof, with a dichloro sulphur-bridged compound of formula Cl-R-Cl or

in the ratio of 2 moles of dithiophosphoric acid, or salt thereof, to one mole of dichloro sulphur-bridged compound to obtain compounds of the formula:-

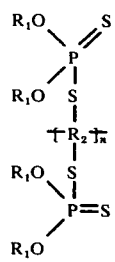

in which R, $R_1$, $R_2$ and n have the same significance as above.

Alternatively the dithiophosphoric acid, or salt thereof, and the dichloro sulphur-bridged compound may be reacted in a 1:1 mole ratio to leave unreacted chlorine. The latter may then be reacted with a metal derivative of the nucleophilic group A. In yet another, and preferable, alternative the derivative of the nucleophilic group may be reacted in 1:1 mole ratio with the dichloro sulphur-bridged compound and the resulting intermediate then reacted with the dithiophosphoric acid, or metal or amine salt thereof.

The dichloro sulphur-bridged starting materials of the process of the present invention may be prepared by reacting sulphur dichloride with an excess, for example 5 mole excess, of the unsaturated ring compound from which R is derived, preferably in an inert solvent at a temperature of about −20° C to give a dichloro derivative Cl-R-Cl. Details of this preparation are given in J. Org. Chem. 33, P. 2627 incorporated herein by reference. In a similar manner, but employing substantially equimolar quantities of reactants, the substantially intermolecularly sulphur-bridged hydrocarbon ring structure $[R_2]_n$ may be formed. In the latter case a higher reaction temperature may be used if desired.

In some cases the additive prepared in the process of the present invention described above may contain residual reactive ethylenically unsaturated double bonds, which may be reacted with compounds reactive therewith. Such compounds reacting with residual unsaturation include sulphur, phosphorus pentasulphide, mercaptans, phenols, thiocyanate anions, thiophenols and carboxylic acids. Specific examples of such compounds are mercaptans and carboxylic acids containing from 1 to 16 carbon atoms; phenol (unsubstituted) and thiophenol (unsubstituted). The foregoing compounds may be reacted with the residual unsaturation at a temperature of from 50° to 200° C and in the case of sulphur, thiocyanates and phosphorus pentasulphide no catalyst is required. In the case of the other compounds however, it may be desirable to use a catalyst known to promote their reaction with ethylenically unsaturated double bonds, such as mineral acids or Lewis acid catalysts such as boron trifluoride or the etherate or phenolate complex thereof.

In the context of the present invention the term lubricating composition comprises compositions to be employed directly as lubricants. In this case the novel compounds of the present invention will normally comprise from 0.1 to 10%, more preferably 0.25 to 5%, by weight of the lubricating composition. However, the term lubricating composition also embraces the materials known in the art as concentrate and packages, i.e., concentrated solutions in lubricating oil, optionally together with one or more conventional additives, intended to be diluted with further quantities of oil to form the final lubricant. In this case the novel compounds of the present invention may be present in a wide range of proportions e.g. 10 to 90%. In general such concentrated solutions will normally contain from 20 to 50% by weight of the novel compounds of the present invention. The lubricating oil used in the lubricants, or the concentrates or packages, may be any of the well known oils of appropriate viscosity characteristics and may include synthetic oils.

It will be understood that the lubricants of the present invention may also contain, if desired, conventional lubricant additives such as ancillary antioxidants and antiwear additives (preferably ashless), corrosion inhibitors, dispersants, particularly dispersants of the succinimide type, detergents, thickeners, pour-point depressants and viscosity index improvers. Numerous examples of such conventional additives are described in U.K. Patent Specification No. 1,205,177 and the various documents referred to therein.

The present invention will now be illustrated by the following Examples.

EXAMPLE 1

Preparation of 2,9-dichloro-13-thiabicyclo [8,2,1]-5-tridecene:

A mixture of 1,5,9-cyclododecatriene (810g., 5 mole) in methylene dichloride (500 ml) in a glass flask fitted with stirrer and nitrogen cover system was cooled to −20° C. A solution of sulphur dichloride (103g., 1 mole) in methylene dichloride (500 ml) was added over about one hour. The mixture was allowed to warm to room temperature overnight, filtered and stripped on a rotary evaporator to give a dark liquid with some brown deposit. The liquid solidified overnight, was recrystallised from petroleum ether (boiling point 62°–68° C) to give a light brown solid which was dried in a desiccator. 82.0g (30.9%) of crude product was obtained containing 30.2% Cl (Calc. 26.8) and 12.0% S (Calc. 12.07%). A sample was dissolved in petroleum ether (boiling point 62.68° C), treated with activated charcoal, recrystallised twice to yield a compound having a melting point of 124° – 126° C.

EXAMPLE 2

Example 1 was repeated using the following technique:

A mixture of 1,5,9-cyclododecatriene (972g., 6 mole) in methylene dichloride (2500 ml) in a glass flask fitted with stirrer and nitrogen cover system was cooled to −20° C. A solution of sulphur dichloride (123.6g., 1.2 mole) in methylene dichloride (600 ml) was slowly added over about five hours. The mixture was allowed to warm to room temperature overnight, filtered and stripped on a rotary evaporator to give a dark liquid with some brown deposit. The liquid solidified overnight, was recrystallised from petroleum ether (boiling point 62°–68° C) to give a light brown solid which was dried in a Vacuum Oven; 201.4g. (63.2%) of crude product was obtained containing 22.2% Cl (Calc. 26.8) and 11.2% S (Calc. 12.07%).

EXAMPLE 3

Preparation of Bis (O,O'-ditridecyl dithiophosphato)-13-thiabicyclo [8,2,1] tridec-5-ene.

2,9-Dichloro-13-thiabicyclo[8,2,1]-5-tridecene intermediate was prepared substantially as in Example 1 or 2 yielding a crude product containing 25.9% Cl (Calc. 26.8) and 11.5% S (Calc. 12.07).

Triethylamine (44.4g., 0.44 mole) was added to ditridecyl dithiophosphoric acid (241g., 0.44 mole) in toluene (100 ml) with a slight exotherm. 2,9-Dichloro-13-thiabicyclo [8,2,1]-5-tridecene (53g., 0.2 mole), (crude product prepared as above) in toluene (200 ml) was then added, and the temperature raised to 80° to 100° C which temperature was maintained for 5 hours. The solution was washed twice with 10% $NaHCO_3$ (100 ml) then washed twice with water (150 ml). After drying over magnesium sulphate, the product was filtered and the solvent removed on a rotary evaporator to yield 211.2g (89.0%) of a cloudy liquid containing 4.88% P (Calc. 5.25%), 12.6% S (Calc. 13.5%) and 0.25% Cl (Calc. 0.00%). The product was found to be soluble in mineral oil.

EXAMPLES 4 to 17

The preparations were carried out substantially as in Example 3. The experimental details of Examples 4 to 17 are given in the following Table I.

In the formation of dithiophosphate compounds there occurs as a side reaction the formation of a proportion of trithiopyrophosphate derivatives and this normally leads to measured yields being high. It will be noted that in some cases the measured yields exceed 100%.

TABLE 1

PREPARATION OF "THIABICYCLO" DITHIOPHOSPHATE DERIVATIVES

| | REACTANTS (MOLES) | | | REACTION | | DTPA ALKYL GROUP | ANALYSIS | | |
|---|---|---|---|---|---|---|---|---|---|
| | DCTT | DTPA | BASE | TIME | TEMP. °C | | %S | %P | %Cl |
| EXAMPLE 4 | 0.15 | 0.33 | 0.33[1] | 6 Hrs | 80–100° | Diisobutyl | 22.03 (23.7) | 8.35 (9.18) | 0.35 (0) |
| EXAMPLE 5 | 0.2 | 0.44 | 0.44[1] | 5 Hrs | 80–100° | Di(1-methyl heptyl) | 15.8 (17.8) | 6.39 (6.90) | 1.31 (0.00) |
| EXAMPLE 6 | 0.2 | 0.44 | 0.44[1] | 5 Hrs | 90° | Tridecyl/p-cresyl | 13.76 (16.4) | 6.28 (6.4) | 0.58 (0.00) |
| EXAMPLE 7 | 0.2 | 0.44 | 0.44[2] | 3 Hrs | 90° | Di-p-nonyl phenyl | 11.07 (12.7) | 4.26 (4.92) | 0.42 (0.00) |
| EXAMPLE 8 | 0.2 | 0.2 | 0.2[1] | 3 Hrs | 90° | Di-p-nonyl phenyl | | | |
| | | 0.22 | 0.22[1] | 3 Hrs | 90° | Diisobutyl | 15.37 (16.35) | 5.74 (6.3) | 0.53 (0.00) |
| EXAMPLE 9 | 0.25 | 0.6 | 0.6[1] | 3 Hrs | 80° | Diisopropyl | 27.3 (25.7) | 9.57 (9.97) | 1.17 (0.00) |
| EXAMPLE 10 | 0.2 | 0.2 | 0.2[1] | 3 Hrs | 90–93° | Dicapryl | | | |
| | | 0.3 | 0.3[1] | 3 Hrs | 65–68° | Diallyl | 20.4 (21.3) | 7.48 (8.25) | 1.93 (0.00) |
| EXAMPLE 11 | 0.25[3] | 0.3 | 0.3[1] | 4 Hrs | 90° | Ditridecyl | 12.9 (12.3) | 4.03 (3.98) | 0.90 (0.00) |
| EXAMPLE 12 | 0.25[4] | 0.3 | 0.3[1] | 3 Hrs | 90° | Ditridecyl | 14.4 (17.2) | 4.11 (4.16) | 1.05 (0.00) |
| EXAMPLE 13 | 0.25[5] | 0.3 | 0.3[1] | 3 Hrs | 90° | Diisobutyl | 19.8 (20.1) | 3.67 (4.87) | 0.48 (0.00) |
| EXAMPLE 14 | 0.25[6] | 0.3 | 0.3[1] | 3 Hrs | 90° | Ditridecyl | 11.94 (13.5) | 3.91 (4.55) | 0.77 (0.00) |
| EXAMPLE 15 | 0.25[7] | 0.3 | 0.3[1] | 4 Hrs | 90° | Ditridecyl | 10.83 (12.8) | 4.39 (4.15) | 0.4 (0.00) |
| EXAMPLE 16 | 0.25[8] | 0.3 | 0.3[1] | 4 Hrs | 91–93° | Diisobutyl | 19.3 (17.9) | 6.29 (5.78) | 1.2 (0.00) |
| EXAMPLE 17 | 0.25[9] | 0.3 | 0.3[1] | 3 Hrs | 90° | Di-p-nonyl phenyl | 11.6 (12.5) | 3.88 (4.04) | 1.18 (0) |

| | Acidity mgKOH/g | % YIELD | COMMENTS |
|---|---|---|---|
| EXAMPLE 4 | 0 | 70.0 | |
| EXAMPLE 5 | 0 | 116.0 | |
| EXAMPLE 6 | 0 | 86.2 | |
| EXAMPLE 7 | 0 | 88.0 | |
| EXAMPLE 8 | 0 | 102.0 | Two-Stage process |
| EXAMPLE 9 | 0 | 78.5 | Owing to the high chlorine level in the initial product it was retreated with 0.2 mole of DTPA/Et₃N salt for 3 hrs at 80° C. Product was then washed dried and stripped on rotary evaporator as previously and the quoted analysis and yield obtained |
| EXAMPLE 10 | 0 | 92.0 | Two-Stage process |

TABLE 1-continued
PREPARATION OF "THIABICYCLO" DITHIOPHOSPHATE DERIVATIVES

| REACTANTS (MOLES) | | | REACTION | | DTPA ALKYL | ANALYSIS | | |
|---|---|---|---|---|---|---|---|---|
| DCTT | DTPA | BASE | TIME | TEMP. °C | GROUP | %S | %P | %Cl |
| EXAMPLE 11 | | 0 | | 91.5 | | | | |
| EXAMPLE 12 | | 0 | | 127.0 | | | | |
| EXAMPLE 13 | | 0 | | 79.4 | The final product was retreated with 0.2 moles sodium n-dodecyl mercaptide in toluene for 7 hrs at 90–100° C. Then washed with water and dried over magnesium sulphate, then stripped under high vacuum. | | | |
| EXAMPLE 14 | | 0 | | 124.0 | | | | |
| EXAMPLE 15 | | 0 | | 118.0 | | | | |
| EXAMPLE 16 | | 0 | | 95.9 | | | | |
| EXAMPLE 17 | | 0 | | 97.1 | %N 1.85 (1.82) | | | |

Note

DCTT is 2,9-dichloro-13-thiabicyclo [8,2,1] -5-tridecene DTPA is a dithiophosphoric acid.
1. Triethylamine
2. Pyridine
3. The compound denoted as DCTT[3] in Table 1 was prepared as follows:

Phenol (23.5g., 0.25 mole) was dissolved in 450 ml toluene and heated to 65°–70° C. Sodium (6.0g., 0.25 mole) was added and the mixture heated to 95°–98° C for two and a half hours. The reaction mixture was allowed to cool overnight. 2,9-dichloro-13-thiabicyclo [8,2,1] -5-tridecene (66.3g., 0.25 mole) (crude product prepared as in Example 1 or 2) was dissolved in toluene (200 ml) and added to the reaction mixture described above, with exothermic reaction. The temperature was raised to 90°–92° C and maintained for three hours, yielding a yellow solution which was cooled, then washed with water (2 × 200 ml). The product solution was filtered through phase separation paper.

4. The compound denoted as DCTT[4] in Table 1 was prepared as follows:

2,9-dichloro-13-thiabicyclo[8,2,1] -5-tridecene (66.3g., 0.25. mole) (crude product prepared as in Example 1 or 2) was dissolved in methyl ethyl ketone (700 ml). Potassium thiocyanate (24.3g., 0.25 mole) was added and the temperature was raised to 80° C and maintained for three hours, yielding a solution containing a white precipitate. The product was stripped of solvent on a rotary evaporator to near dryness. Water (200 ml) was added to dissolve the precipitate and the stripping was continued to remove all the methyl ethyl ketone. This stage was repeated with a further quantity of water (100 ml). The product was allowed to cool then dissolved in toluene (200 ml), when two phases separated. The organic phase was washed with water (200 ml) then filtered through phase Separation paper.

5. The compound denoted as DCTT[5] in Table 1 was prepared as follows:

Sodium (5.75g., 0.25 mole) was added to a mixture of n-dodecyl mercaptan (50.5g., 0.25 mole) and toluene (200 ml). The reaction was started at a temperature of 50° C then heated to 80° C, yielding a white solution. The temperature was raised to 100° C and maintained for fifteen hours. A further quantity of toluene (100 ml) was added and the temperature raised to 100° C for a further eighteen hours.

2,9-dichloro-thiabicyclo [8,2,1] -5-tridecene (66.3g., 0.25 mole) (crude product prepared as in Example 1 or 2) was dissolved in toluene (200 ml) and the product described above was added over a period of two hours at 50° C without exothermic reaction. The temperature was raised to 100° C and maintained for three hours. The product was cooled, filtered and washed with water (100 ml).

6. The compound denoted as DCTT[6] in Table 1 was prepared as follows:

Sodium cyanide (12.3g., 0.25 mole), ethanol (300 ml) and 2,9-dichloro-13-thiabicyclo [8,2,1] -5-tridecene (66.3g., 0.25 mole) (crude product prepared as in Example 1 or 2) were mixed together with exothermic reaction. A water bath was placed under the flask containing the mixture and the temperature maintained itself at 30° C for half an hour. The temperature was then raised to 75° C for three hours. The product was cooled and water (600 ml) was then added to precipitate the product which was filtered off.

7. The compound denoted as DCTT[7] in Table 1 was prepared as follows:

Anhydrous sodium acetate (15.0g., 0.25 mole), glacial acetic acid (200 ml) and 2,9-dichloro-13-thiabicyclo [8,2,1]-5-tridecene (66.3g., 0.25 mole) (crude product from Example 1 or 2) were mixed together with exothermic reaction. The temperature was raised to 100° C and maintained for 2 hours. The product was cooled overnight, then filtered and water (600 ml) was then added to the filtrate. A brown liquid was precipitated which was extracted with toluene. The organic phase was washed twice with water (150 ml) then dried over magnesium sulphate, then filtered.

8. The compound denoted as DCTT[8] in Table 1 was prepared as follows:

Toluene (100 ml) and 1-hexanol (25.5g., 0.25 mole) were mixed and sodium (6.0g., 0.25 mole) added at 47° C. The mixture was then heated at 93°–96° C for 3½ hours and after cooling 2,9-dichloro-13-thiabicyclo [8,2,1]tridec-5-ene (66.3g., 0.25 mole) dissolved in toluene (200 ml) was added. This mixture was then heated to 91°–94° C for 3 hours, cooled washed with water and filtered through phase separation paper.

The compound denoted as DCTT[9] in Table 1 was prepared as follows:

2,9-Dichloro-13-thiabicyclo [8,2,1]-5-tridecene (66.3g., 0.25 mole), methyl ethyl ketone (700 ml) and potassium cyanate (20.2g., 0.25 mole) were mixed and heated to reflux (82° C) for a total of 25½ hours. The reaction mixture was then stripped of solvent on a rotary evaporator and when almost dry water (700 ml) was added and the stripping continued. Further water 300 ml) was added together with toluene (950 ml) to dissolve the mixture and the organic layer separated off and filtered through phase separating paper.

EXAMPLE 18

Dichloromethane (1 l) was cooled to 0° to −5° C and cis, trans, trans-1,5,9-cyclododecatriene (324g., 2.0 mole) and sulphur dichloride (206g., 2.0 mole) were added simultaneously from 2 dropping funnels at equimolar rates. The temperature was kept below 0° C during the addition, but thereafter the resulting orange liquid was allowed to warm up to room temperature. It was then heated at 45° C for 4 hours and solvent removed on a rotary evaporator to yield a semi-solid brown mass, which was stirred with petroleum ether (B.Pt. 62°–68° C) and filtered to yield an off-white solid. This solid was again treated with the petroleum ether, at reflux, and filtered to yield a polymeric solid which was insoluble in toluene, benzene, methyl ethyl ketone and water, which had a melting point of 144° C and which contained 12.7%S and 23.8% Cl (calc. 12.07% and 26.8% respectively).

The polymeric solid (132.5g., 0.5 mole) and toluene (500 ml) were mixed and O,O'-ditridecyl dithiophosphoric acid (521g., 1.0 mole) added. Triethylamine (101g., 1.0 mole) was then added and the mixture heated at reflux (113° C) for 3 hours. The reaction mixture, after cooling, was filtered and the filtrate washed with 10% NaHCO$_3$ and water, and then was dried over anhydrous MgSO$_4$. The solvent was removed on a rotary evaporator. The resulting product was found to have a relatively high chlorine content and to be incompletely soluble in mineral oil. It was therefore re-treated with the dithiophosphoric acid triethylamine salt (300g., 0.2 mole) for 5 hours at 70° C in petroleum ether (B.Pt. 62°–68° C) solvent. The washing and stripping procedure was then repeated to yield a fully oil-soluble final product containing 4.84%P, 11.08%S and 0.6%Cl (calc. 4.94%, 12.77% and 0 respectively).

The compounds prepared in Examples 4 to 17 were tested to determine their antiwear/load carrying, antioxidant and corrosion inhibiting properties.

The load carrying properties were determined using the Timken O.K. Load Test according to the Institute of Petroleum test method IP 240/69T. The test blends consisted of the test additive dissolved in 150 Solvent Neutral mineral oil, the former being in an amount to provide 0.072% by weight phosphorus in the test blend.

To determine the antioxidant properties, Rotary Bomb Tests were carried out according to the Institute of Petroleum test method IP 229/68T. The test blends consisted of 2.0% by weight of the test additive dissolved in 500 Solvent Neutral mineral oil.

The corrosion inhibiting properties were determined using the Copper Strip Test according to the Institute of Petroleum test method IP 154/69 with the minor difference that the test was conducted for three hours at a test temperature of 120° C. The test blends consisted of the test compound dissolved in 500 Solvent Neutral mineral oil, the former being in an amount to provide 0.072% by weight phosphorus in the test blend.

Results of these tests are given in the following Table 2.

The I.R. Spectrum for each of the Examples was determined and found to be consistent with the expected product.

TABLE 2

PRODUCT TEST DATA

| EXAMPLE NO | COMPOUND | ROTARY BOMB[1] TEST (minutes) | TIMKEN OK LOAD[2] lb | % | COPPER STRIP TEST |
|---|---|---|---|---|---|
| 3 | Bis(O,O'ditridecyl dithiophosphato)-13-thiabicyclo [8,2,1] tridec-5-ene | 150 | | | |
| 4 | Bis(diisobutyl dithiophosphato)-13-thiabicyclo[8,2,1] tridec-5-ene | 295* | 24 | 1.47 | — |
| 5 | Bis(dicapryl dithiophosphato)-13-thiabicyclo [8,2,1] tridec-5-ene | 255 | 24 | 0.86 | — |
| 6 | Bis(tridecyl/p-cresyl dithiophosphato)-13-thiabicyclo [8,2,1] tridec-5-ene | 162* | 50 | 1.13 | 3b |
| 7 | Bis(di-p-nonyl phenyl dithiophosphato)-13-thiabicyclo [8,2,1] tridec-5-ene | 61* | 40 | 1.15 | 3b |
| 8 | 2-(di-p-nonyl phenyl dithiophosphato)-9-(diisobutyl dithiophosphato-13-thiabicyclo [8,2,1] tridec-5-ene | 80 | 55 | 1.69 | 4a |
| 9 | 2,9-(diisopropyl dithiophosphato)-13-thiabicyclo [8,2,1] tridec-5-ene | 106 | 40 | 1.25 | 4c |
| 10 | 2(di-allyl dithiophosphato)-9-(dicapryl dithiophosphato)-13-thiabicyclo [8,2,1] tridec-5-ene | 115 | 40 | 0.75 | 2a/2b |
| 11 | 2-(ditridecyl dithiophosphato)-9-phenoxy-13-thiabicyclo [8,2,1] tridec-5-ene | 50 | 35 | 0.96 | 3b |
| 12 | 2-(O,O'ditridecyl dithiophosphato)-9-isothiocyanato)-13-thiabicyclo [8,2,1] tridec-5-ene | 130 | 24 | 1.79 | 4a |
| 13 | 2-(diisobutyl dithiophosphato)-9-dodecyl thio -13- thiabicyclo [8,2,1] tridec-5-ene | 90 | 40 | 1.75 | 4c |
| 14 | 2-(ditridecyl dithiophosphato)-9-cyano-13-thiabicyclo [8,2,1] tridec-5-ene | 375 | 18 | 1.95 | 1a |
| 15 | 2-acetoxy-9 (ditridecyl dithiophosphato)-13-thiabicyclo [8,2,1] tridec-5-ene | 148* | 35 | 1.84 | 4c |
| 16 | 2-(diisobutyl dithiophosphato)-9-hexanoxy-13-thiabicyclo [8,2,1] tridec-5-ene | 175* | 24 | 1.64 | 4c |
| 17 | 2-(di-p-nonylphenyl dithiophosphato)-9-isocyanate-13-thiabicyclo [8,2,1] | 195 | 30 | 1.15 | 3b |

TABLE 2-continued

| | | PRODUCT TEST DATA | | | |
|---|---|---|---|---|---|
| EXAMPLE NO | COMPOUND | ROTARY BOMB[1] TEST (minutes) | TIMKEN OK LOAD[2] lb | % | COPPER STRIP TEST |
| | tridec-5-ene | 127 | 30 | 1.85 | 3b |

[1]Time to 25 psi loss unless * then time to induction break
[2]Rings used for this test were supplied by The Timken Company, Canton, Ohio, U.S.A.

We claim:

1. A lubricating composition consisting essentially of a lubricating oil and a minor effective amount of a compound of the formula

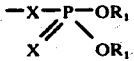

(I) (II)

wherein in Formula (I) R is the residue of an intramolecular sulphur bridged hydrocarbon ring containing 12 carbon atoms or wherein in Formula (II) $\{R_2\}_n$ is a polymer comprising the residue of a plurality of substantially intermolecularly sulphur-bridged hydrocarbon rings each containing 12 carbon atoms, n being the degree of polymerisation; each $R_1$ being independently selected from the group consisting of alkyl, alkenyl, aryl, alkaryl and aralkyl groups and each $R_1$ containing from 2 to 18 carbon atoms; and A is a nucleophilic group selected from the group consisting of -CN,-NCO,-NCS,

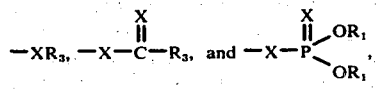

wherein each $R_1$ is as above, X is oxygen or sulphur and $R_3$ is an alkyl group containing 1–12 carbon atoms or a phenyl group.

2. The lubricating composition of claim 1 containing from 0.1 to 10% by weight of the compound of Formula (I) or Formula (II).

3. The lubricating composition of claim 1 containing from 0.25 to 5% by weight of the compound of Formula (I) or Formula (II).

4. The lubricating composition of claim 1, wherein each $R_1$ of said compound is selected from the group consisting of alkyl-substituted phenyl groups containing from 7 to 18 carbon atoms and alkyl groups containing from 3 to 18 carbon atoms.

5. The lubricating composition of claim 1, wherein each $R_1$ is an alkyl group containing from 3 to 10 carbon atoms.

6. The lubricating composition of claim 1, wherein R or $R_2$ of said compound is derived from cis, trans, trans-1,5,9-cyclododecatriene.

7. The lubricating composition of claim 1, wherein group A of said compound has the formula $$-X-P(=X)(OR_1)(OR_1)$$

in which both groups X are sulphur atoms.

* * * * *

UNITED STATES PATENT AND TRADEMARK OFFICE
CERTIFICATE OF CORRECTION

PATENT NO. : 4,002,568
DATED : January 11, 1977
INVENTOR(S) : Gerald John Joseph Jayne et al It is certified that error appears in the above-identified patent and that said Letters Patent are hereby corrected as shown below:

Column 3, lines 10-20 - delete present formula and insert:

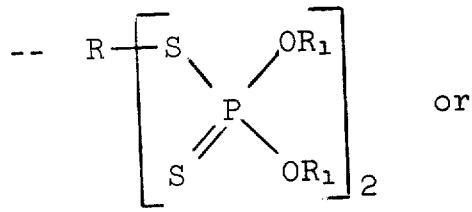 or 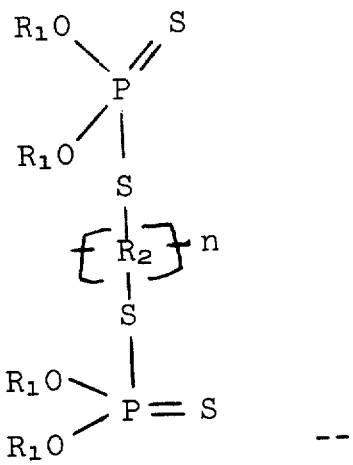

Table 1-continued, bridging Columns 7-8 - delete present headings and insert:

-- Acidity mgKOH/g    % Yield    Comments --

Signed and Sealed this

Twenty-ninth Day of March 1977

[SEAL]

Attest:

RUTH C. MASON
Attesting Officer

C. MARSHALL DANN
Commissioner of Patents and Trademarks